United States Patent [19]
Campbell et al.

[11] Patent Number: 5,932,192
[45] Date of Patent: *Aug. 3, 1999

[54] LOWER ASTRINGENT TWO COMPONENT STANNOUS AND POTASSIUM SALT CONTAINING DENTIFRICE

[75] Inventors: Shannon Karin Campbell, Piscataway; Steven Wade Fisher, Middlesex; Edward Albert Tavss, Kendall Park; Marilou Theresa Joziak, South River, all of N.J.

[73] Assignee: Colgate-Palmolive Company, New York, N.Y.

[ * ] Notice: This patent is subject to a terminal disclaimer.

[21] Appl. No.: 08/841,509

[22] Filed: Apr. 23, 1997

[51] Int. Cl.⁶ .................................. A61K 7/16; A61K 7/18
[52] U.S. Cl. ............................................. 424/52; 424/49
[58] Field of Search ........................................ 424/49–88

[56] References Cited

U.S. PATENT DOCUMENTS

| | | |
|---|---|---|
| 3,863,006 | 1/1975 | Hodosh ....................... 424/49 |
| 5,213,790 | 5/1993 | Lukacovic et al. ............... 424/52 |
| 5,240,696 | 8/1993 | Van Der Ouderaa et al. ...... 424/49 |
| 5,240,697 | 8/1993 | Norfleet et al. ................. 424/52 |
| 5,260,062 | 11/1993 | Gaffar ......................... 424/49 |
| 5,352,439 | 10/1994 | Norfleet et al. ................. 424/52 |
| 5,503,823 | 4/1996 | Norfleet et al. ................. 424/52 |
| 5,505,933 | 4/1996 | Norfleet et al. ................. 424/52 |
| 5,674,474 | 10/1997 | Fisher et al. ................... 424/52 |
| 5,690,912 | 11/1997 | Campbell et al. ............... 404/52 |
| 5,693,314 | 12/1997 | Campbell et al. ............... 404/49 |

FOREIGN PATENT DOCUMENTS

| | | |
|---|---|---|
| 0 222 603 | 5/1987 | European Pat. Off. . |
| 0278744 | 8/1988 | European Pat. Off. ......... A61K 7/16 |
| 0 390 456 | 10/1990 | European Pat. Off. . |
| 0 696 450 | 2/1996 | European Pat. Off. . |
| 8702890 | 5/1987 | WIPO ............................ A61K 7/16 |
| 9325184 | 12/1993 | WIPO ............................ A61K 7/16 |
| 95 28911 | 11/1995 | WIPO . |

*Primary Examiner*—Shep K. Rose
*Attorney, Agent, or Firm*—Henry S. Goldfine

[57] ABSTRACT

A two component desensitizing dentifrice composition, having reduced astringency and enhanced taste is disclosed which comprises a first aqueous dentifrice component containing a desensitizing potassium salt, having a water content greater than 44% by weight; and a second anhydrous dentifrice component containing a stannous salt, the first and second dentifrice components being maintained separate from each other until dispensed for application to the teeth.

10 Claims, No Drawings

LOWER ASTRINGENT TWO COMPONENT STANNOUS AND POTASSIUM SALT CONTAINING DENTIFRICE

BACKGROUND OF THE INVENTION

1. Field of the Invention

The present invention relates to a two component dentifrice composition, having a first component containing stannous fluoride and a second component containing potassium nitrate and more particularly to such a composition which exhibits lower astringency and enhanced taste.

2. The Prior Art

Incorporation of stannous compounds into oral health products for the purpose of achieving particular clinical benefits such as caries prevention, plaque control and the reduction of gingivitis is known in the art. In spite of these benefits, stannous compounds are not widely used in oral care formulations as stannous compounds react with water and other common oral care ingredients to form insoluble tin and other undesirable products. Further, stannous ions impart an astringent, bitter, sour metallic taste to dentifrices, which is not consumer acceptable and which is particularly unacceptable to children, astringency being defined as a drying of the oral mucosa, which results in a puckering or styptic sensation.

Copending U.S. patent application Ser. No. 08/287,371, filed Aug. 8, 1994, discloses a dual component dental desensitizing composition comprised of a stannous salt-containing anhydrous gel, and a potassium salt-containing aqueous dentifrice, which are admixed immediately prior to application to the teeth to avoid any appreciable formation of insoluble tin or reaction product of tin and hence providing less than the formulated quantity of tin salt, such as $SnF_2$, and less than the formulated quantity of potassium salt, such as $KNO_3$, to the oral surfaces. However, the composition retains the astringent, sour, metallic taste attributes associated with stannous compounds. Accordingly, there is a need in the art for a dental desensitizing composition containing tin salts, which does not have such negative attributes.

SUMMARY OF THE INVENTION

The present invention encompasses a two component desensitizing dentifrice composition, having a first anhydrous dentifrice component containing a stannous salt, such as stannous fluoride, and a second aqueous dentifrice component containing a potassium salt, such as potassium nitrate; the first and second components being separated prior to use, wherein, the water content within the potassium salt containing dentifrice component is at least 44% and preferably at least 48% by weight, so that the water content of the first and second components is at least 22% by weight when the two components are combined immediately prior to application to the teeth; whereby unexpectedly, the astringency, sourness and bitterness of the stannous salt is significantly reduced and the overall taste enhanced.

DESCRIPTION OF THE PREFERRED EMBODIMENTS

In use, the components of the two component dentifrice of the present invention, are combined in approximately equal weight proportions so that only about one-half of the concentration of any particular ingredient, within either component, will be present when the components are combined and applied to the teeth, as by brushing.

In the preparation of the potassium salt desensitizing component of the present invention, the potassium salt ingredient is incorporated within a dentifrice vehicle, which contains water, humectant, surfactant and a polishing agent. The humectant is generally a mixture of humectants, such as glycerol, sorbitol and polyethylene glycol of molecular weight in the range of 200–1000, but other mixtures of humectants and single humectants may also be employed. The humectant content within the potassium salt containing dentifrice component is in the range about of 10% to about 80% by weight and preferably about 40 to about 50% by weight. The water content which is critical to the practice of the present invention is at least about 44% to about 60%, and preferably at least about 48% by weight.

The source of desensitizing potassium ion is generally a water soluble potassium salt including potassium nitrate, potassium citrate, potassium chloride, potassium bicarbonate and potassium oxalate, potassium nitrate being preferred. The potassium salt is generally incorporated in the compositions of the present invention at a concentration of about 2 to about 15% by weight and preferably about 5 to about 12% by weight.

Inorganic thickeners may be included in the dentifrices in which potassium salts are included as an ingredient thickeners include fumed silicas such as Cabosil available from Cabot Corporation, and thickening silicas including those available from Crosfield Chemicals designated Sorbosil TC-15 or Sylox 15 from W.R. Grace.

Organic thickeners of natural and synthetic gums as colloids may also be incorporated in the dentifrice composition of the present invention in which potassium salts are an ingredient. Examples of such thickeners are carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

The organic thickener may be incorporated in the compositions of the present invention at a concentration of about 0.1 to about 3% by weight and preferably about 0.5 to about 1% by weight.

Surface active agents may be incorporated in the dentifrices in which a desensitizing potassium salt is included as an ingredient to provide foaming properties and include anionic, nonionic or ampholytic compounds, anionic compounds being preferred. Suitable examples of anionic surfactants are higher alkyl sulfates such as potassium or sodium lauryl sulfate which is preferred, higher fatty acid monoglyceride monosulfates, such as the salt of the monosulfated monoglyceride of hydrogenated coconut oil fatty acids, alkyl aryl sulfonates such as sodium dodecyl benzene sulfonate, higher fatty sulfoacetates, higher fatty acid esters of 1,2 dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the salts of N-lauroyl, N-myristoyl, or N-palmitoyl sarcosine.

The surface active agent is generally present in the potassium salt dentifrice compositions of the present invention at a concentration of about 0.5 to about 5.0% by weight.

Abrasives may be incorporated in the potassium salt dentifrice component of the present invention and preferred abrasives are siliceous materials, such as silica, and will normally have a mean particle size up to about 10 microns and a very high surface area e.g. in the range of 150–750 square meters/gram. A preferred silica is a precipitated amorphous hydrated silica, such as Sorbosil AC-35, marketed by Crosfield Chemicals, or Zeodent 115 from Huber Company but other abrasives may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, zirconium silicate, calcined alumina and bentonite.

The concentration of abrasive in the potassium salt desensitizing dentifrice component composition of the present invention will normally be in the range of 2 to about 40% by weight and preferably 5 to 20% by weight.

Other ingredients which may be incorporated in the potassium salt desensitizing component of the present invention, include pigment, sweetener, flavor and preservative. In white dental cream formulations, the pigment will be titanium dioxide, rutile, and the proportion thereof will normally be in the range of 0.5 to 1% by weight, preferably 0.75 to 1.25% by weight. The sweetener content will normally be that of an artificial or synthetic sweetener and the normal proportion thereof present will be in the range of 0.1 to 1% by weight, preferably 0.3 to 0.5% by weight. The flavor content, which is preferably of a mixed peppermint/menthol flavor, will usually be in the range of 0.5 to 2% by weight, preferably 0.5 to 1.5% by weight. F.D. & C Grade dyes may be used in appropriate amounts to provide desired colors. The contents of other components or adjuvants of the potassium salt containing dentifrice component will normally not exceed 10% by weight, often will be less than 5% by weight, and can be as low as 0%.

To prepare the desensitizing potassium salt dentifrice component of the present invention, the humectant and gelling agent are dispersed in a conventional mixer until the mixture becomes a slurry which is smooth in appearance, after which water is added. This mixture may be heated to 100–110° F. and mixed for 10 to 30 minutes producing a homogeneous gel phase. The potassium salt is added and mixed for 20 minutes or until completely dissolved. Sweetener and color are added and mixed for 20 minutes. The mixture is transferred to a vacuum mixer. The abrasive is then added and mixed for 10 to 30 minutes at high speed under a vacuum in the range of 5 to 100 millimeter of mercury pressure, preferably 5 to 50 mm Hg, providing a homogenous mixture. The surfactant and flavor are then added to the paste which is followed by mixing another 10 to 20 minutes under vacuum of 5 to 50 mm Hg. The resultant product is a stable desensitizing dentifrice of a texture like that of normal toothpastes or gels having a pH in the range of 5 to 8, preferably 6.5 to 7.5, e.g., 7, and of satisfactory flavor.

In the preparation of the second dentifrice component which contains a stannous salt, such as $SnF_2$, due to the chemical instability of such salts in aqueous solutions, the salt is formulated as an ingredient of a nonaqueous gel, wherein anhydrous glycerine is a carrier for the stannous salt.

The stannous salt gel component of the present invention is generally comprised of about 0.10 to about 2.0% by weight of the stannous salt. In the preparation of anhydrous gels containing $SnF_2$, the gel contains about 0.30 to about 0.9% by weight $SnF_2$, preferably 0.35 to 0.85% by weight; about 87 to about 97% by weight anhydrous glycerine, preferably about 90 to about 95% by weight; and about 2.0 to about 10.0% by weight of polyethylene glycol having an average molecular weight of 1000, preferably about 5.0 to about 8.0% by weight.

Although $SnF_2$ is preferred for use in the practice of the invention, stannous salts other than $SnF_2$ may be used in the practice of the present invention. Examples of these stannous salts include stannous chloride, stannous phosphate, stannous citrate and stannous gluconate.

Also included in the compositions of the present invention is an effective flavoring amount of a flavor compatible and stable with the stannous salt. The flavor ingredient constitutes about 0.05 to about 1% by weight and preferably about 0.1 to about 0.5% by weight of the gel composition. Suitable flavoring constituents are flavoring oils, e.g. oils of spearmint, peppermint, wintergreen, clove, methyl salicylate and menthol.

Thickening agents may optionally be included in the stannous salt gels of the present invention at a concentration of about 0.01 to about 0.8% by weight. Suitable thickening agents include hydroxyethyl cellulose and water soluble salts of cellulose ethers such as sodium carboxymethyl cellulose and sodium carboxymethyl hydroxyethylcellulose as well as natural gums, such as xanthan gum.

The anhydrous stannous salt gel of this invention may be prepared by suspending the salt, flavor and polyethylene glycol 1000 in anhydrous glycerine heated to a temperature of 45 to 140° C. by mixing in any suitable mixer, such as a Lightening mixer for about 30 minutes until a homogenous solution is formed. A substantially rigid non-fluid gel product is obtained upon cooling.

Any convenient means for effecting the separation of the potassium salt containing dentifrice from the stannous salt containing gel component before use can be utilized. For example, a single container can be compartmentalized so that a $SnF_2$ containing gel and a potassium salt containing dentifrice are housed in separate compartments and are not admixed until applied to the teeth. For example, segregated dentifrice components can be housed in a common container and be separated from one another by a barrier, such as a wall integrally formed within the container which prevents mixing prior to the compositions being dispensed. Such technology is known in the art, an example of which is disclosed in copending U.S. patent application Ser. No. 08/287,371, filed Aug. 8, 1994, which is incorporated herein by reference. Alternatively, the $SnF_2$ containing component and the $KNO_3$ containing component can be housed in separate containers from which the respective phases are dispensed for admixture just prior to use.

The following example is further illustrative of the present invention, but it is understood that the invention is not limited thereto. All amounts and proportions referred to herein and the appended claims are by weight.

EXAMPLE

The astringency and other taste attributes (i.e. sourness, bitterness and overall taste) of a two component dentifrice composition of the present invention was assessed by a panel of 56 human subjects, screened for good health and the absence of oral disease, in a monadic, blind panel test. The first component of the assessed dentifrice composition was an anhydrous $SnF_2$ gel designated Gel A, the formulation of which is presented in Table I, below. The second component of the assessed dentifrice composition was a potassium nitrate paste designated Paste A, its formulation is presented in Table II, below.

TABLE I

Formulation of SnF$_2$ Gel A*

| Ingredients | % by Weight |
|---|---|
| Glycerine | 92.3989 |
| Polyethylene Glycol 1000 | 6.0000 |
| Xanthan Gum | 0.3000 |
| Stannous Fluoride | 0.8000 |
| Flavor | 0.5000 |
| Dye | 0.0011 |
| Total | 100.0000 |

*Note: The level of each ingredient in the combination of the two component dentifrice is equal to approximately 50% of that shown within this one component.

Gel A was prepared by first premixing the glycerine, flavor and polyethylene glycol 1000 at 100° C. for 30 minutes to form a homogenous solution. The solution was then mixed with the SnF$_2$ for 30 minutes at a speed of 800 revolutions/min with a Lightning mixer. Subsequently, the xanthan gum was added and mixing was continued for another 10 minutes. The dye was added and mixing was continued for another 2 minutes. When the formulation cooled, the desired gel formed.

TABLE II

Formulation of Potassium Nitrate Desensitizing Paste A*

| Ingredients | % by Weight |
|---|---|
| Water | 52.1500 |
| Sorbitol | 0.0000 |
| Silica Abrasive | 18.0000 |
| Glycerine | 11.0000 |
| Potassium Nitrate | 10.0000 |
| Polyethylene Glycol 600 | 3.0000 |
| Sodium Lauryl Sulfate | 2.4000 |
| Silica Thickener | 1.0000 |
| Xanthan Gum | 0.8500 |
| Flavor | 1.0000 |
| Sodium Saccharin | 0.4000 |
| Titanium Dioxide | 0.2000 |
| Total | 100.0000 |

*Note: The level of each ingredient in the combination of the two component dentifrice is equal to approximately 50% of that shown within this one component.

Paste A was prepared by dispersing the formula quantities of glycerine, sorbitol, polyethylene glycol 600, and xanthan gum in a conventional mixer until the mixture became a slurry, which was smooth in appearance; water was added and mixed for 10 to 30 minutes producing a homogeneous gel phase in which the potassium nitrate was dispersed. Titanium dioxide and sodium saccharin were added and the resulting product was mixed for 20 minutes and transferred to a vacuum mixer. The siliceous thickener and abrasive were then added and mixed for 10 to 30 minutes at high speed under a vacuum of about 50 mm Hg, providing a homogenous paste mixture. The sodium lauryl sulfate and flavor were then added to the paste, followed by mixing another 20 minutes under vacuum of 50 mm Hg.

For purposes of comparison, the procedure of the Example was repeated with a gel component, designated Gel B having substantially the same composition as Gel A, and a potassium nitrate containing dentifrice component, designated Paste B containing substantially less water than Paste A. The formulations of comparative Gel B and comparative Paste B are shown below in Tables III and IV, respectively.

TABLE III

Comparative Gel B Formulation

| Ingredients | % by Weight |
|---|---|
| Glycerine | 91.6989 |
| Polyethylene Glycol 1000 | 7.0000 |
| Stannous Fluoride | 0.8000 |
| Flavor | 0.5000 |
| Dye | 0.0011 |
| Total | 100.0000 |

TABLE IV

Comparative Paste B Formulation*

| Ingredients | % by Weight |
|---|---|
| Water | 28.0000 |
| Sorbitol | 21.2000 |
| Silica Abrasive | 18.0000 |
| Glycerine | 17.5000 |
| Potassium Nitrate | 10.0000 |
| Polyethylene Glycol 600 | 0.0000 |
| Sodium Lauryl Sulfate | 1.2000 |
| Silica Thickener | 1.0000 |
| Xanthan Gum | 1.0000 |
| Flavor | 1.5000 |
| Sodium Saccharin | 0.4000 |
| Titanium Dioxide | 0.2000 |
| Total | 100.0000 |

The combined gel and paste desensitizing dentifrice composition was assessed by each panelist, in the morning prior to having brushed their teeth that day, by each panelist coextruding a ribbon weighing approximately 1 to 1.5 grams, composed of equal parts of an unidentified anhydrous stannous fluoride gel and an unidentified aqueous potassium nitrate containing paste, which were housed in separate compartments of a dual chamber plastic tube, onto a toothbrush for application to the panelists teeth. Each panelist brushed for 45 seconds with this unidentified combination, which was in fact the combined Gel A and Paste A components, rinsed for 10 seconds and immediately thereafter rated the composition for overall taste acceptability (using the 9 level scale presented in Table V, below) and for the compositions taste attributes of astringency, sourness and bitterness (using the 9 level scale presented in Table VI, below). After a waiting period of at least four (4) hours, each panelist was given an approximately 1 to 1.5 gram sample of a second unidentified two component gel/paste dentifrice, which was in fact the combined Gel B and Paste B components, and repeated the 45 second brushing, 10 second rinse and recorded the overall taste and the taste attributes of astringency, sourness and bitterness levels. The mean astringency, sourness, bitterness and overall taste acceptability results of the panelists' assessments of the Gel A/Paste A and Gel B/Paste B combinations are recorded in Table VII, below. Note, as specified in Tables V and VI, respectively, a higher rating is desirable for overall taste acceptability, but a lower rating is desirable for the attributes of astringency, sourness and bitterness.

TABLE V

Scale for Overall Taste Acceptability Measurement

| Assessment Rating | Taste |
| --- | --- |
| 1 | Extremely unacceptable |
| 2 | Moderately unacceptable |
| 3 | Neither unacceptable nor acceptable |
| 4 | Moderately acceptable |
| 5 | Extremely acceptable |

TABLE VI

Scale for Measurement of the Taste Attributes
of Astringency, Sourness and Bitterness Measurement

| Assessment Rating | Intensity of Taste Attribute |
| --- | --- |
| 1 | Not present - zero intensity |
| 2 | Slightly present - slight intensity |
| 3 | Moderately present - moderate intensity |
| 4 | Very present - very intensive taste effect |
| 5 | Extremely present - extremely intensive taste effect |

TABLE VII

Mean Astringency, Sourness,
Bitterness, and Overall Taste Assessment Ratings

| | Combination | |
| --- | --- | --- |
| Taste Attribute Rated | Gel A and Paste A | Gel B and Paste B |
| Astringency | 4.2 | 5.3 |
| Sourness | 2.9 | 4.1 |
| Bitterness | 3.3 | 4.3 |
| Overall Taste Acceptability | 5.0 | 4.0 |

Referring to Table VII, the astringency, sourness and bitterness rating of the combined Gel A and Paste A dentifrice, of the present invention, were found, at a 90% confidence level, to be statistically different and less astringent, sour and bitter than the comparative combined Gel B and Paste B dentifrice, while the overall taste acceptability of the combined Gel A and Paste A dentifrice was enhanced.

What is claimed is:

1. A two component desensitizing dentifrice composition which exhibits lessened astringency comprising a first anhydrous dentifrice component containing a stannous salt and a second aqueous dentifrice component containing a desensitizing potassium salt having therein a water content of at least about 44% by weight; the first and second dentifrice components being maintained separate from each other until dispensed for application to teeth requiring relief from dentine hypersensitivity, whereby the astringency of the combined dentifrice is reduced and the taste is enhanced when the components are combined for brushing.

2. The composition of claim 1 wherein the potassium salt is potassium nitrate.

3. The composition of claim 1 wherein the stannous salt is stannous fluoride.

4. The composition of claim 1 wherein the second dentifrice component is an aqueous dentifrice containing potassium nitrate and the first dentifrice component is an anhydrous gel containing stannous fluoride.

5. The composition of claim 1 wherein the second dentifrice component contains at least about 48% water by weight.

6. A method for treating dentin hypersensitivity which comprises preparing a two component dentifrice; the first component being an anhydrous dentifrice component containing a stannous salt; the second dentifrice component being an aqueous dentifrice component containing a desensitizing potassium salt and having a water content of at least about 44% by weight; maintaining the first and second dentifrice components separate from each other until dispensed for application to teeth; thereafter combining the two components to obtain a composition in which the user experiences reduced astringency.

7. The composition of claim 6 wherein the potassium salt is potassium nitrate.

8. The composition of claim 6 wherein the stannous salt is stannous fluoride.

9. The composition of claim 6 wherein the second dentifrice component is an aqueous dentifrice containing potassium nitrate and the first dentifrice is an anhydrous gel containing stannous fluoride.

10. The composition of claim 6 wherein the second dentifrice component contains at least about 48% water by weight.

* * * * *